(12) United States Patent
Czub et al.

(10) Patent No.: US 7,491,493 B2
(45) Date of Patent: Feb. 17, 2009

(54) METHOD AND KIT FOR MOLECULAR IDENTIFICATION OF SMALLPOX

(76) Inventors: Markus Czub, 1015 rue Arlington Piece T2420, Winnipeg Manitoba (CA) R3E 3P6; Allen Grolla, 1015 rue Arlington Piece T2420, Winnipeg Manitoba (CA) R3E 3P6

( * ) Notice: Subject to any disclaimer, the term of this patent is extended or adjusted under 35 U.S.C. 154(b) by 71 days.

(21) Appl. No.: 10/553,453

(22) PCT Filed: Apr. 19, 2004

(86) PCT No.: PCT/CA2004/000591

§ 371 (c)(1),
(2), (4) Date: Sep. 28, 2006

(87) PCT Pub. No.: WO2004/092420

PCT Pub. Date: Oct. 28, 2004

(65) Prior Publication Data

US 2007/0054263 A1  Mar. 8, 2007

Related U.S. Application Data

(60) Provisional application No. 60/463,333, filed on Apr. 17, 2003.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .............. 435/6, 435/91.2; 536/24.33
See application file for complete search history.

(56) References Cited

FOREIGN PATENT DOCUMENTS

EP  0 753 581  1/1997

OTHER PUBLICATIONS

Loparev, V et al. Detection and differntiation of old world orthpoxviruses: Restriction fragmetn length polymorphism of the crmB gene region. J Clin Microbiol., vol. 39, No. 1, pp. 94-100, 2001.*

Lowe, T et al. A computer program for selection of oligonucleotide primers for polymerase chain reaction. Nucleic Acids Research, vol. 18, No. 1, pp. 1757-1761, 1990.*

Loparev V N et al "Detection and Differentiation of old world orthopoxviruses: restriction fragment length polymorphism of the crmB gene region" Journal of Clinical Microbiology Jan. 2001, vol. 39, No. 1, Jan. 2001 pp. 94-100.

Ropp S L et al "PCR Strategy for identification and differentiation of small pox and other orthopoxviruses" Journal of Clinical Microbiology, Washington DC vol. 33 No. 8 Aug. 1995 pp. 2069-2076.

Meyer H. et al "Gene for A-type inclusion body protein is useful for a polymerase chain reaction assay to differentiate orthopoxviruses" Journal of Virological Methods, Amsterdam, vol. 64, No. 2, Mar. 1997 pp. 217-221.

Database Biosis "online" Biosciences Information Service, Philadelphia PA US 2003, Nie Z et al Detection and differentiation of variola virus from other orthopoxviruses using RFLP of the complement regulatory protein gene.

* cited by examiner

*Primary Examiner*—Suryaprabha Chunduru
(74) *Attorney, Agent, or Firm*—Ade & Company Inc.; Michael R. Williams (57) ABSTRACT

Novel PCR based assays to detect Orthopoxvirus DNA have been developed which when tested under simulated clinical conditions have proven to be very sensitive, rapid and robust. Furthermore, artificial templates have been constructed which can be used as positive controls in the RFLP analysis necessary to differentiate variola and monkeypox viruses from the Orthopoxvirus species that normally cause relatively insignificant disease in man. These assays will provide a lab that has already undertaken the isolation of DNA from a patient sample in biocontainment with a sensitive and controlled assay for the detection and differentiation of human-tropic orthopox viruses.

3 Claims, 4 Drawing Sheets

```
atgc cggtacttat gtatgtgcat tctttatgac atcaactaca aatgatactg
ataaagtaga ttatgaagaa tactctacag agttgattgt aaacacagat agtgaatcga
ctatagacat aatactatct ggatcttcac attcaccgga aactagttct gagaaacctg
attatataaa taattttaat tgctcgttgg tatttgaaat cgcgactccg ggaccaatta
ctgataatgt agaaaatcat acagacactg tcacatacac tagtgatatc attaatacag
taagtacatc atctggagaa tccacaacag acaaga
```

Figure 5a - Variola HA amplicon (SEQ ID No. 5)

```
tacc ggtctcagcg
aatccatctt aacgtcggaa ctaactatta ctatgaatca tacagattgc aatcccgtat
ttcgtgagga atacttctct gtccttaata aggtagcaac ttcaggattt tttacaggag
aaaatagata tcaaaatatt tcaaaggtgt gtactttaaa ttttgagatt aaatgtaata
acaaaggttc ttccttcaaa cagctaacga aagcaaagaa tgatgacggt atgatgtcgc
attcggagac ggtaactcta
```

Figure 5b - Variola crmB amplicon (SEQ ID No. 6)

```
atgcc ggtacttata tatgtgcatt ctttatgaca
tcgactacaa atgatactga taaagtagat tatgaagaat actccataga gttgattgta
aatacagata gtgaatcgac tatagacata atactatctg gatctacacc ggaaactatt
tctgagaaac cagaggatat agataattct aattgctcgt ctgtattcga aatcgcgact
ccggaaccaa ttactgataa tgtagaagac catacagaca ccgtcacata cactagtgat
agcattaata cagtaaatgc atcatctgga gaatccacaa cagacgaga
```

Figure 5c - Monkeypox HA amplicon (SEQ ID No. 7)

```
taccg gtctcagcga atccatctca acgtcggaac
taactattac catgaatcat aaagattgtg atcccgtctt tcgtgcagaa tacttctctg
tccttaataa tgtagcaact tcaggattct ttacaggaga aaatagatat cagaatactt
caaagtatg tactctgaat ttcgagatta aatgtaacaa caaagattca tcttccaaac
agttaacgaa aacaaagaat gatactatca tgccgcattc agagacggt
```

Figure 5d - Monkeypox crmB (SEQ ID No. 8)

SEQUENCE LISTING

<160> NUMBER OF SEQ ID NOS: 25

<210> SEQ ID NO 1
<211> LENGTH: 22
<212> TYPE: DNA
<213> ORGANISM: Artificial
<220> FEATURE:
<223> OTHER INFORMATION: synthetic primer or template

<400> SEQUENCE: 1
atgccggtac ttatgtatgt gc                                    22

```
<210> SEQ ID NO 2
<211> LENGTH: 20
<212> TYPE: DNA
<213> ORGANISM: Artificial
<220> FEATURE:
<223> OTHER INFORMATION: synthetic primer or template

<400> SEQUENCE: 2
tcttgtctgt tgtggattct                                                   20

<210> SEQ ID NO 3
<211> LENGTH: 18
<212> TYPE: DNA
<213> ORGANISM: Artificial
<220> FEATURE:
<223> OTHER INFORMATION: synthetic primer or template

<400> SEQUENCE: 3
taccggtctc agcgaatc                                                     18

<210> SEQ ID NO 4
<211> LENGTH: 20
<212> TYPE: DNA
<213> ORGANISM: Artificial
<220> FEATURE:
<223> OTHER INFORMATION: synthetic primer or template

<400> SEQUENCE: 4
accgtctccg aatgcggcat                                                   20

<210> SEQ ID NO 5
<211> LENGTH: 330
<212> TYPE: DNA
<213> ORGANISM: Artificial
<220> FEATURE:
<223> OTHER INFORMATION: synthetic primer or template

<400> SEQUENCE: 5
atgccggtac ttatgtatgt gcattcttta tgacatcaac tacaaatgat actgataaag       60
tagattatga agaatactct acagagttga ttgtaaacac agatagtgaa tcgactatag      120
acataatact atctggatct tcacattcac cggaaactag ttctgagaaa cctgattata      180
taaataattt taattgctcg ttggtatttg aaatcgcgac tccgggacca attactgata      240
atgtagaaaa tcatacagac actgtcacat acactagtga tatcattaat acagtaagta      300
catcatctgg agaatccaca acagacaaga                                       330

<210> SEQ ID NO 6
<211> LENGTH: 274
<212> TYPE: DNA
<213> ORGANISM: Artificial
<220> FEATURE:
<223> OTHER INFORMATION: synthetic primer or template

<400> SEQUENCE: 6
taccggtctc agcgaatcca tcttaacgtc ggaactaact attactatga atcatacaga       60
ttgcaatccc gtatttcgtg aggaatactt ctctgtcctt aataaggtag caacttcagg      120
attttttaca ggagaaaata gatatcaaaa tatttcaaag gtgtgtactt taaatttga      180 gattaaatgt aataacaaag gttcttcctt caaacagcta acgaaagcaa agaatgatga      240
cggtatgatg tcgcattcgg agacggtaac tcta                                  274
```

```
<210> SEQ ID NO 7
<211> LENGTH: 324
<212> TYPE: DNA
<213> ORGANISM: Artificial
<220> FEATURE:
<223> OTHER INFORMATION: synthetic primer or template

<400> SEQUENCE: 7
atgccggtac ttatatatgt gcattctttta tgacatcgac tacaaatgat actgataaag      60
tagattatga agaatactcc atagagttga ttgtaaatac agatagtgaa tcgactatag     120
acataatact atctggatct acaccggaaa ctatttctga gaaccagag gatatagata     180 attctaattg ctcgtctgta ttcgaaatcg cgactccgga accaattact gataatgtag     240
aagaccatac agacaccgtc acatacacta gtgatagcat taatacagta aatgcatcat     300
ctggagaatc cacaacagac gaga                                            324

<210> SEQ ID NO 8
<211> LENGTH: 264
<212> TYPE: DNA
<213> ORGANISM: Artificial
<220> FEATURE:
<223> OTHER INFORMATION: synthetic primer or template

<400> SEQUENCE: 8
taccggtctc agcgaatcca tctcaacgtc ggaactaact attaccatga atcataaaga      60
ttgtgatccc gtctttcgtg cagaatactt ctctgtcctt aataatgtag caacttcagg     120
attctttaca ggagaaaata gatatcagaa tacttcaaag atatgtactc tgaatttcga     180
gattaaatgt aacaacaaag attcatcttc caaacagtta acgaaaacaa agaatgatac     240
tatcatgccg cattcagaga cggt                                            264

<210> SEQ ID NO 9
<211> LENGTH: 71
<212> TYPE: DNA
<213> ORGANISM: Artificial
<220> FEATURE:
<223> OTHER INFORMATION: synthetic primer or template

<400> SEQUENCE: 9
atgccggtac ttatatatgt gcattctttta tgacatcaag cttgcggccg ctgcagacta      60
caaatgatac t                                                           71

<210> SEQ ID NO 10
<211> LENGTH: 64
<212> TYPE: DNA
<213> ORGANISM: Artificial
<220> FEATURE:
<223> OTHER INFORMATION: synthetic primer or template

<400> SEQUENCE: 10
taccggtctc agcgaatcca tctyaagctt gcggccgctg cagaacgtcg gaactaacta      60
ttac                                                                   64

<210> SEQ ID NO 11
<211> LENGTH: 69
<212> TYPE: DNA
<213> ORGANISM: Artificial
<220> FEATURE:
<223> OTHER INFORMATION: synthetic primer or template

<400> SEQUENCE: 11
```

-continued

```
cgtctctgaa tgcggcatga tagtatcatt ctttgtctgc agcggccgca agctttcgtt    60
aactgtttg                                                             69
```

<210> SEQ ID NO 12
<211> LENGTH: 84
<212> TYPE: DNA
<213> ORGANISM: Artificial
<220> FEATURE:
<223> OTHER INFORMATION: synthetic primer or template

<400> SEQUENCE: 12

```
atgccggtac ttatctatgt gcattcttta tgacatcaac tacaaatgat actaataaag    60
tagattatga agaatactct acag                                            84
```

<210> SEQ ID NO 13
<211> LENGTH: 103
<212> TYPE: DNA
<213> ORGANISM: Artificial
<220> FEATURE:
<223> OTHER INFORMATION: synthetic primer or template

<400> SEQUENCE: 13

```
ctcagaacta gtttccggtg aatgtgaaga tccagatagt attatgtcta tagtcgattc    60
actatctgtg tttacaatca actctgtaga gtattcttca taa                      103
```

<210> SEQ ID NO 14
<211> LENGTH: 103
<212> TYPE: DNA
<213> ORGANISM: Artificial
<220> FEATURE:
<223> OTHER INFORMATION: synthetic primer or template

<400> SEQUENCE: 14

```
caccggaaac tagttctgag aaacctgatt atataaataa ttttaattgc tcgttggtat    60
ttgaaatcgc gactccggga ccaattactg ataatgtaga aaa                      103
```

<210> SEQ ID NO 15
<211> LENGTH: 99
<212> TYPE: DNA
<213> ORGANISM: Artificial
<220> FEATURE:
<223> OTHER INFORMATION: synthetic primer or template

<400> SEQUENCE: 15

```
tcttgtctgt tgtggattct ccagatgatg tacttactgt attaatgata tcactagtta    60
tgtgacagtg tctgtatgat tttctacatt atcagtaat                            99
```

<210> SEQ ID NO 16
<211> LENGTH: 84
<212> TYPE: DNA
<213> ORGANISM: Artificial
<220> FEATURE:
<223> OTHER INFORMATION: synthetic primer or template

<400> SEQUENCE: 16

```
atgccggtac ttatatatgt gcattcttta tgacatcgac tacaaatgat actgataaag    60
tagattatga agaatactcc atag                                            84
```

<210> SEQ ID NO 17
<211> LENGTH: 99
<212> TYPE: DNA
<213> ORGANISM: Artificial

```
<220> FEATURE:
<223> OTHER INFORMATION: synthetic primer or template

<400> SEQUENCE: 17
ctcagaaata gtttccggtg tagatccaga tagtattatg tctatagtcg attcactatc     60
tgtatttaca atcaactcta tggagtattc ttcataatc                            99

<210> SEQ ID NO 18
<211> LENGTH: 102
<212> TYPE: DNA
<213> ORGANISM: Artificial
<220> FEATURE:
<223> OTHER INFORMATION: synthetic primer or template

<400> SEQUENCE: 18
caccggaaac tatttctgag aaaccagagg atatagataa ttctaattgc tcgtctgtat     60
cgaaatcgcg actccggaac caattactga taatgtagaa ga                       102

<210> SEQ ID NO 19
<211> LENGTH: 104
<212> TYPE: DNA
<213> ORGANISM: Artificial
<220> FEATURE:
<223> OTHER INFORMATION: synthetic primer or template

<400> SEQUENCE: 19
tctcgtctgt tgtggattct ccagatgatg catttactgt attaatgcta tcactagtgt     60
atgtgacggt gtctgtatgg tcttctacat tatcagtaat tggt                     104

<210> SEQ ID NO 20
<211> LENGTH: 115
<212> TYPE: DNA
<213> ORGANISM: Artificial
<220> FEATURE:
<223> OTHER INFORMATION: synthetic primer or template

<400> SEQUENCE: 20
taccggtctc agcgaatcca tcttaacgtc ggaactaact attactatga atcatacaga     60
ttgcaatccc gtatttcgtg aggaatactt ctctgtcctt aataaggtag caact         115

<210> SEQ ID NO 21
<211> LENGTH: 112
<212> TYPE: DNA
<213> ORGANISM: Artificial
<220> FEATURE:
<223> OTHER INFORMATION: synthetic primer or template

<400> SEQUENCE: 21
agaacctttg ttattacatt taatctcaaa atttaaagta cacacctttg aaatattttg     60
atatctattt tctcctgtaa aaaatcctga agttgctacc ttattaagga ca            112

<210> SEQ ID NO 22
<211> LENGTH: 114
<212> TYPE: DNA
<213> ORGANISM: Artificial
<220> FEATURE:
<223> OTHER INFORMATION: synthetic primer or template

<400> SEQUENCE: 22
aaatgtaata acaaaggttc ttccttcaaa cagctaacga aagcaaagaa tgatgacggt     60
atgatgtcgc attcggagac ggtaactcta gcgggtgact gtctatctag cgtc          114
```

```
<210> SEQ ID NO 23
<211> LENGTH: 115
<212> TYPE: DNA
<213> ORGANISM: Artificial
<220> FEATURE:
<223> OTHER INFORMATION: synthetic primer or template

<400> SEQUENCE: 23
taccggtctc agcgaatcca tctcaacgtc ggaactaact attaccatga atcataaaga      60
ttgtgatccc gtctttcgtg cagaatactt ctctgtcctt aataatgtag caact          115

<210> SEQ ID NO 24
<211> LENGTH: 113
<212> TYPE: DNA
<213> ORGANISM: Artificial
<220> FEATURE:
<223> OTHER INFORMATION: synthetic primer or template

<400> SEQUENCE: 24
gatgaatctt tgttgttaca tttaatctcg aaattcagag tacatatctt tgaagtattc     60
tgatatctat tttctcctgt aaagaatcct gaagttgcta cattattaag gac            113

<210> SEQ ID NO 25
<211> LENGTH: 110
<212> TYPE: DNA
<213> ORGANISM: Artificial
<220> FEATURE:
<223> OTHER INFORMATION: synthetic primer or template

<400> SEQUENCE: 25
aaatgtaaca acaaagattc atcttccaaa cagttaacga aaacaaagaa tgatactatc     60
atgccgcatt cagagacggt aactctagtg ggcgactgtc tatctagcgt                110
```

METHOD AND KIT FOR MOLECULAR IDENTIFICATION OF SMALLPOX

PRIOR APPLICATION INFORMATION

This application claims priority on U.S. Ser. No. 60/463,333, filed Apr. 17, 2003.

FIELD OF THE INVENTION

The present invention relates generally to the field of pathogen identification.

BACKGROUND OF THE INVENTION

Currently, international concern is heightened regarding the use of Smallpox virus as a bioterrorism agent. Smallpox is a disease caused by an infection with the variola virus, a member of the genus Orthopoxvirus. The last naturally occurring case of Smallpox was reported in Somalia in 1977. Since recommendations for routine Smallpox vaccination were rescinded in North America and most of Europe in 1971, and the effectiveness of vaccination appears to last only 10 years, much of the world population is currently susceptible to infection. During the Smallpox era, overall mortality rates were approximately 30%. Death usually occurred late in the first week or during the second week of illness and was usually attributed to overwhelming viremia. The virus is highly transmissible from person-to-person and infected individuals may, in turn, infect tens to hundreds of susceptible contacts.

The only acknowledged stockpiles of variola virus, the causative agent of smallpox, are those maintained in the USA and Russia (Henderson, D. A. et al. JAMA 281,2127-2137 (1999)). The recent anthrax attack on the USA, however, has renewed fears that additional stockpiles do exist and could be used as a bioterrorist weapon on a now largely susceptible population. The diagnosis of ordinary-type smallpox was relatively easy when endemic, and was based on the distribution and evolution of the rash. However, in non-endemic regions, smallpox could sometimes be confused with chickenpox which is caused by a herpesvirus (varicella) (Fields' virology, Knipe, D. M., Howley, P. M. (eds)-4th ed., 2001).

Other members of OPV that can cause clinical disease in man and for which discrimination is needed are Monkeypox virus (MPXV), which produces a clinically similar, although usually less severe disease that has, until recently, been restricted to western sub-Saharan Africa (Centers for Disease Control and Prevention. 2003, Morb. Mortal. Wkly. Rep. 52:537-540; Esposito and Fenner, 2002. Poxviruses, p. 2885-2921. In Knipe et al., Fields' virology, 4th ed. Lippincott Williams & Wilkins, Philadelphia, Pa.). Vaccinia virus (VACV) and Cowpox virus (CWPX) can both infect humans, normally resulting in a mild disease (Esposito and Fenner, 2002), although VACV has been known to cause severe, even fatal complications following vaccination (Henderson et al. 1999, JAMA 281:2127-2137). It is unclear if Camelpox virus (CMPX) causes disease in humans but it's genome has recently been recognized as being the most closely related to VARV (Gubser and Smith, 2002, J. Gen. Virol. 83:855-872) and concerns raised over possible genetic manipulation to a human virulent strain.

Ideally, diagnostic tests for OPV must be rapid, sensitive and discriminatory for the OPV that cause significant disease in humans. Very rapid methods have been described such as real-time 5' nuclease PCR (polymerase chain reaction)(Espy et al., 2002, Mayo Clin. Proc. 77:624-628; Hazelton and Gelderblom, 2003, Emerg. Infect. Dis. 9:294-303; Ibrahim et al., 2003, J. Clin. Microbiol. 41:3835-3839; Ibrahim et al., 1997, Mol. Cell. Probes 11:143-147; Kulesh et al., 2004, J Clin Microbiol. February; 42(2):601-9; Mackay et al., 2002, Nucleic Acids Res. 30:1292-1305; Nitsche et al., 2004, Clin Microbiol. March; 42(3):1207-13) and PCR followed by oligonucleotide microarray hybridization (Ibrahim et al., 1998, Anal. Chem. 70: 2013-2017; Lapa et al., 2002, J. Clin. Microbiol. 40:753-757.) but these techniques require specialized instrumentation that may not always be available. PCR based assays have been described to detect and differentiate OPV infections and when combined with sequencing or restriction fragment length polymorphism (RFLP) analysis of products can offer a high degree of sensitivity and discrimination and can be accomplished in many existing laboratories (Loparev et al., 2001, J. Clin. Microbiol. 39:94-100; Meyer et al., 1997, J. Virol. Methods 64:217-221; Neubauer et al., 1998, J. Virol. Methods 74:201-207; Ropp et al., 1995, J. Clin. Microbiol. 33:2069-2076).

For most laboratories, the lack of positive controls for VARV is a significant concern for both the amplification step and subsequent RFLP analysis. The development of molecular biological tests as diagnostic tools in infectious diseases began, for the most part, after nations had destroyed their VARV stocks or deposited them at the two reference centers. Access to this material is extremely limited and impossible for most organizations making controlled testing procedures difficult or impossible to put in place.

As discussed above, when faced with a potential smallpox or monkeypox outbreak, time is of the essence. Clearly, a quick and easy method of determining if orthopoxvirus is present within a sample and identifying the orthopoxvirus is needed. Diagnostic tests need to be available to rapidly and accurately detect and differentiate these pathogens, especially VARV and MPXV, in clinical material for appropriate public health actions to be initiated: To address this need we have developed rapid and highly sensitive PCR-RFLP assays targeted to the OPV hemagglutinin (HA) and cytokine response modifier B (crmB) genes, complete with synthetic positive controls, suitable for use in most routinely equipped laboratories.

SUMMARY OF THE INVENTION

According to a first aspect of the invention, there is provided a method of detecting and identifying an orthopoxvirus within a sample comprising:

adding to the sample reagents for nucleic acid amplification and at least one pair of primers capable of amplifying at least one region of the orthopoxvirus genome, said region of the orthopoxvirus genome selected from the group consisting of HA and crmB;

incubating the sample under conditions suitable for nucleic acid amplification thereby producing an amplicon if the sample contains orthopoxvirus;

adding at least one restriction enzyme selected from the group consisting of: Nla III, Sau 3AI, Spe I, Dra I, Hpa I, Ssp I, Alw 44I and combinations thereof; and determining if restriction enzyme digestion of an amplicon has occurred.

According to a second aspect of the invention, there is provided a pair of primers for detecting orthopoxvirus in a sample comprising 12 or more consecutive nucleotides of ATGCCGGTACTTATGTATGTGC (SPOXHA5, SEQ ID NO: 1) and 12 or more consecutive nucleotides of TCT-TGTCTGTTGTGGATTCT (SPOXHA3, SEQ ID NO: 2) or 12 or more consecutive nucleotides of TACCGGTCTCAGC- GAATC (SPOXcrmB5, SEQ ID NO: 3) and 12 or more consecutive nucleotides of ACCGTCTCCGAATGCGGCAT (SPOXcrmB3, SEQ ID NO: 4).

According to a third aspect of the invention, there is provided a kit for detecting and identifying orthopoxvirus comprising:

at least one pair of primers selected from the group consisting of 12 or more consecutive nucleotides of ATGCCGGTACTTATGTATGTGC (SPOXHA5, SEQ ID NO: 1) and 12 or more consecutive nucleotides of TCTTGTCTGTTGTGGATTCT (SPOXHA3, SEQ ID NO: 2); and 12 or more consecutive nucleotides of TACCGGTCTCAGCGAATC (SPOXcrmB5, SEQ ID NO: 3) and 12 or more consecutive nucleotides of ACCGTCTCCGAATGCGGCAT (SPOXcrmB3, SEQ ID NO: 4).

BRIEF DESCRIPTION OF THE DRAWINGS

FIG. 1 Schematic representation of restriction enzyme sites used for RFLP analysis of Orthopoxvirus PCR generated amplicons. Open bars represent the amplicons produced by the HA and crmB primer sets designed for this study. a, Sequence of primers for HA amplification corresponded to base pairs 151327-151347 (SpoxHA5) and 151656-151637 (SpoxHA3) of variola major strain (Bangladesh 1975) GenBank accession # L22579. Amplicons generated using these primers were used in RFLP analysis using Sau 3AI (black arrows) and Spe I (open arrows). These two enzymes were sufficient to differentiate VARV, MPXV and CMLV from each other as well as from VACV or CPXV which produce identical fragments in this assay. b, Sequence of primers for crmB amplification corresponded to base pairs 183227-183244 (SpoxcrmB5) and 183493-183474 (SpoxcrmB3) of variola major strain (Bangladesh 1975). Amplicons generated using these primers were used in RFLP analysis with Dra I (black arrow), and Nla III(diagonally striped arrow). These two restriction enzyme digests allow VARV and MPXV derived amplicons to be identified and distinguished from other OPVsequences. Approximate size of RFLP generated fragments are shown in the table to the right.

FIG. 2. Determination of level of sensitivity using a VACV stock dilution a. PCR results for VACV DNA directly purified from dilutions of virus made in MEM media. The last dilution where crmB amplicon was detectable was in the $10^{-9}$ sample corresponding to approximately 0.0003 pfu detection limit. The HA amplicon was lastly produced in the $10^{-8}$ dilution, or an approximately 0.003 pfu detection limit. b. Absorption of VACV to SW-13 monolayer resulted in amplicon being last produced in the $10^{-7}$ and $10^{-6}$ dilution for crmB and HA respectively. This corresponds to 0.003 and 0.03 pfu detection limit under these conditions. Marker (M) is 100 bp ladder from Invitrogen (Burlington, Ontario, Canada), the 100 to 400 bp bands are present on gel. Negative control lane control is denoted by H.

FIG. 4. PCR/RFLP analysis of OPV included in ENIVD panel. a. Top panel shows the result of amplification using crmB primer set. Panels at middle and bottom show RFLP analysis of amplicons using Dra I and Nla III, respectively. (1. VARV crmB, 2. VARV crmB+19 bp, 3. MPXV crmB, 4. MPXV crmB+19 bp, 5. MPXV*, 6. CMPX*, 7. CWPX 81/02*, 8. VACV Modified Ankarra*, 9. VACV*, 10. CWPX Brighton Red*. 11. VACV MVA, 12. VACV T7, 13. VACV Conn-Master 17633) b. Top panel shows the result of amplification using the HA primer set. Panels at the middle and bottom show RFLP analysis of amplicons using Sau 3AI and Spe I respectively. (1. VARV HA, 2. VARV HA+19 bp, 3. MPXV HA, 4. MPXV HA+19 bp, 5. MPXV*, 6. CMPX*, 7. CWPX 81/02*, 8. VACV Modified Ankarra*, 9. VACV*, 10. CWPX Brighton Red*. 11. VACV MVA, 12. VACV T7, 13. VACV Conn-Master 17633). Samples marked with * provided through ENIVD panel, remaining samples provided by NML.

FIG. 5. Sequences of artificial templates for producing amplicons corresponding to Variola HA (FIG. 5a, SEQ ID No. 5), Variola crmB (FIG. 5b, SEQ ID No. 6), Monkeypox HA (FIG. 5c, SEQ ID No. 7) and Monkeypox crmB (FIG. 5d, SEQ ID No. 8).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "amplification reaction mixture" or "amplification mixture" refers to an aqueous solution comprising the various reagents used to amplify a target nucleic acid. These include but are by no means limited to enzymes, aqueous buffers, salts, target nucleic acid and nucleoside triphosphates.

As used herein, "isolated" or "substantially pure", when referring to nucleic acids, refers to those which have been purified away from other cellular components and/or contaminants by standard techniques, for example, column chromatography, CsCl banding, and alkaline/SDS treatment as well as other techniques well known in the art.

As used herein, "nucleotide polymerase" refers to enzymes that are capable of catalyzing the synthesis of DNA or RNA from nucleoside triphosphate precursors.

As used herein, "primer" refers to an oligonucleotide capable of acting as a point of initiation of DNA synthesis under conditions in which synthesis of a primer extension product complementary to a nucleic acid strand is initiated.

As used herein, "orthopoxvirus" refers to for example but by no means limited to variola, monkeypox, camelpox, vaccinia and/or cowpox viruses.

Proper annealing conditions depend, for example, on the length of the primer or probe, the base composition of said primer or probe and the number of mismatches present and their relative position.

Variola virus is considered an "A" list biological agent of high bioweapon capability and as such, rapid, sensitive and controlled diagnostic assays are needed to confirm any putative clinical cases. We developed two polymerase chain reaction—restriction fragment length polymorphism (PCR-RFLP) based assays to detect variola virus and differentiate it from the clinically similar monkeypox virus and from the related vaccinia and camelpox viruses, utilizing artificially generated RFLP positive controls in place of the unavailable variola and monkeypox virus genomes. Our assays were capable of detecting the presence of less than 10 plaqueforming units (pfu) of vaccinia virus and could prove to be valuable to those institutions where variola and monkeypox positive controls are unavailable for testing of clinical samples.

Figure 1:
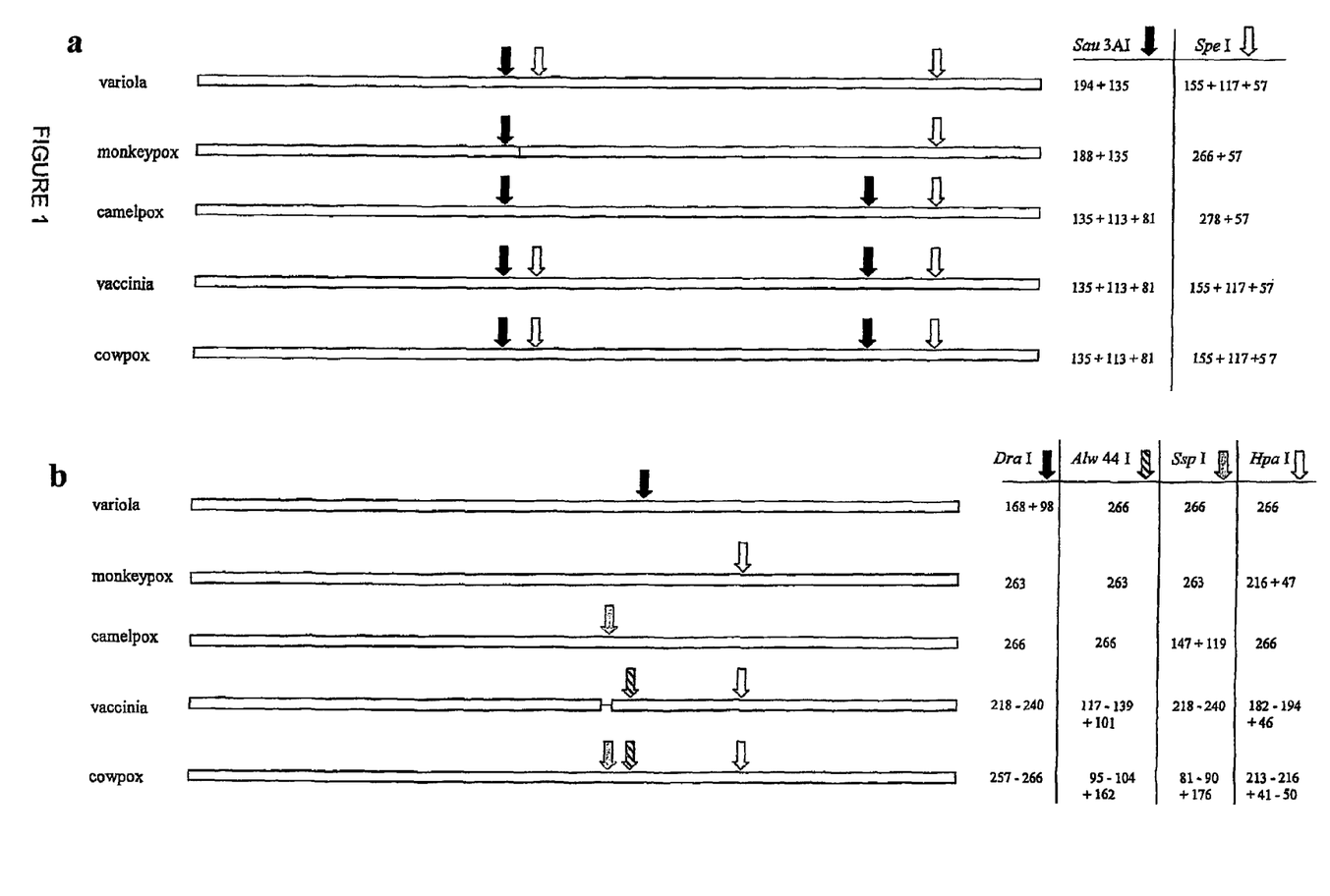

The invention comprises a method of detecting orthopoxvirus within a sample comprising providing primers capable of amplifying a region of the orthopoxvirus genome within the HA gene including restriction enzyme sites for Sau3AI and SpeI and/or primers capable of amplifying a region of the orthopoxvirus genome within the crmB gene including restriction enzyme sites for DraI, Alw44I, SspI and HpaI, as shown in FIG. 1. As will be appreciated by one of skill in the art, a wide variety of primers spanning this region and capable of amplifying genomic DNA from at least one of the orthopoxviruses may be used. The sample and the primers are then incubated under conditions suitable for nucleic acid amplification as discussed below. The resulting amplicon(s) are then digested with at least the respective restriction enzymes listed above and the digestion of the amplicon(s) is determined, for example, visually, by DNA electrophoresis, although other suitable methods known in the art for detecting restriction enzyme cleavage, for example, absence of fluorescence quenching may also be used. As shown in FIG. 1, the restriction enzyme digestion pattern can then be used to identify the orthopoxvirus, if present within the sample.

In another embodiment, the primer pairs comprise 12 or more consecutive nucleotides of ATGCCGGTACTTATGTATGTGC (nucleotides 151327-151347, SPOXHA5, SEQ ID NO: 1) and 12 or more consecutive nucleotides of TCTTGTCTGTTGTGGATTCT (nucleotides 151656-151637, SPOXHA3, SEQ ID NO: 2) for amplification of the region of the HA gene; and 12 or more consecutive nucleotides of TACCGGTCTCAGCGAATC (nucleotides 183227-183244, SPOXcrmB5, SEQ ID NO: 3) and 12 or more consecutive nucleotides of ACCGTCTCCGAATGCGGCAT (nucleotides 183493-183474, SPOXcrmB3, SEQ ID NO: 4) for amplification of the region of the crmB gene.

In other embodiments, the primer pairs may comprise 13 or more, 14 or more, or 15 or more consecutive nucleotides of ATGCCGGTACTTATGTATGTGC (SPOXHA5, SEQ ID NO: 1) and 13 or more, 14 or more, or 15 or more consecutive nucleotides of TCTTGTCTGTTGTGGATTCT (SPOXHA3, SEQ ID NO: 2) for amplification of the region of the HA gene; and/or 13 or more, 14 or more, or 15 or more consecutive nucleotides of TACCGGTCTCAGCGAATC (SPOXcrmB5, SEQ ID NO: 3) and 13 or more, 14 or more, or 15 or more consecutive nucleotides of ACCGTCTCCGAATGCGGCAT (SPOXcrmB3, SEQ ID NO: 4) for amplification of the region of the crmB gene.

In another embodiment, the primer pairs consist essentially of 12 or more consecutive nucleotides of ATGCCGGTACTTATGTATGTGC (SPOXHA5, SEQ ID NO: 1) and 12 or more consecutive nucleotides of TCTTGTCTGTTGTGGATTCT (SPOXHA3, SEQ ID NO: 2) for amplification of the region of the HA gene; and 12 or more consecutive nucleotides of TACCGGTCTCAGCGAATC (SPOXcrmB5, SEQ ID NO: 3) and 12 or more consecutive nucleotides of ACCGTCTCCGAATGCGGCAT (SPOXcrmB3, SEQ ID NO: 4) for amplification of the region of the crmB gene.

In other embodiments, the primer pairs consist essentially of 13 or more, 14 or more, or 15 or more consecutive nucleotides of ATGCCGGTACTTATGTATGTGC (SPOXHA5, SEQ ID NO: 1) and 13 or more, 14 or more, or 15 or more consecutive nucleotides of TCTTGTCTGTTGTGGATTCT (SPOXHA3, SEQ ID NO: 2) for amplification of the region of the HA gene; and/or 13 or more, 14 or more, or 15 or more consecutive nucleotides of TACCGGTCTCAGCGAATC (SPOXcrmB5, SEQ ID NO: 3) and 13 or more, 14 or more, or 15 or more consecutive nucleotides of ACCGTCTCCGAATGCGGCAT (SPOXcrmB3, SEQ ID NO: 4) for amplification of the region of the crmB gene.

As will be known to one of skill in the art, DNA amplification involves allowing two primers to anneal to opposite strands of a template DNA in an amplification mixture and allowing extension of the primers. This process is repeated several times, thereby producing an amplification product. The PCR process is discussed in detail in for example U.S. Pat. No. 4,199,559, U.S. Pat. No. 4,683,195 and U.S. Pat. No. 4,683,202, which are incorporated herein by reference.

To begin the PCR process, the target nucleic acid in the sample is denatured, typically by heating. Once the strands are separated, the next step involves hybridizing the separated strands with the amplification primers. The primers are then extended to form complementary copies of the target strands, and the cycle of denaturation, hybridization and extension is repeated as many times as necessary to obtain the desired amount of amplified nucleic acid.

Template-dependent extension of primers in PCR is catalyzed by a polymerizing agent in the presence of adequate amounts of four deoxyribonucleotide triphosphates in a reaction medium. Suitable polymerizing agents are enzymes known to catalyze template-dependent DNA synthesis. For example, if the template is RNA, a suitable polymerizing agent to convert RNA to cDNA is reverse transcriptase, such as avian myeloblastosis virus RT or Murine Moloney Leukemia Virus RT. If the template is DNA, suitable polymerases include for example *E. coli* DNA polymerase I, the Klenow fragment of DNA polymerase I, $T_4$ DNA polymerase, Hot Tub® and Taq polymerase.

Figure 2:
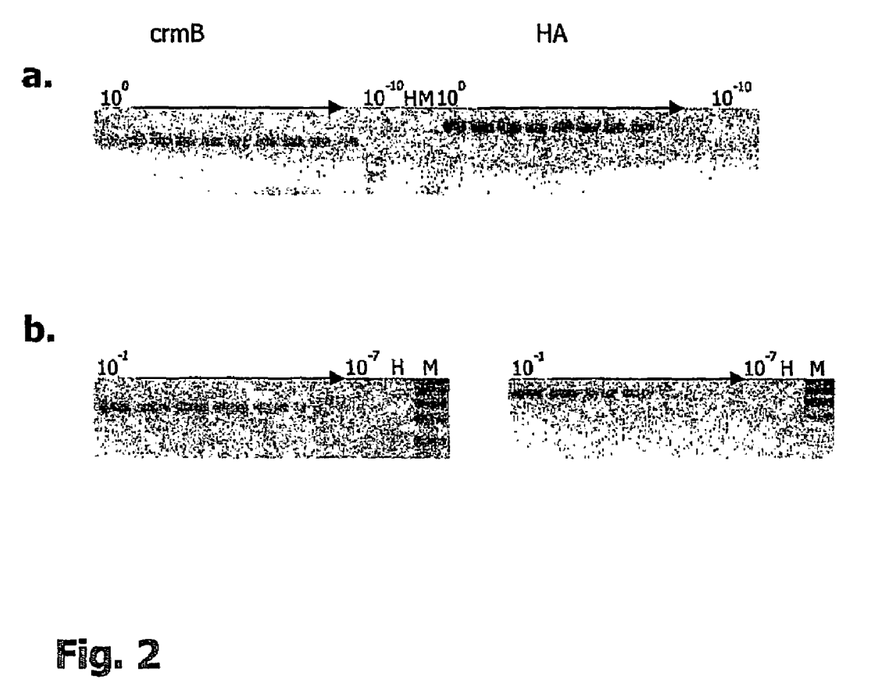

Thus, in one embodiment, primer pairs corresponding to SPOXHA5 and SPOXHA3 and/or SPOXcrmB5 and SPOXcrmB3 are mixed with a sample from a patient suspected of or at risk of orthopoxvirus infection. It is of note that these primers are described herein for illustrative purposes and other suitable primer pairs as discussed above may also be used. Reagents needed for nucleic acid amplification, discussed above, are added to the sample and the sample is incubated under conditions suitable for nucleic acid amplification, for example, an initial inactivation at 95° C., 40 cycles of 45 seconds at 95° C., 45 seconds at 50° C. and 90 seconds at 72° C., followed by a final extension at 72° C. for 5 minutes, although other suitable incubation temperatures and times may also be used. If orthopoxvirus DNA is present within the sample, an amplicon will have been generated as a result of nucleic acid amplification. In some embodiments, as discussed above, positive controls may be added or incubated as controls for nucleic acid amplification and restriction enzyme digestion, as discussed below. Restriction enzymes, selected from the group consisting of Sau 3AI, Nla III, Spe I, Dra I, Alw 44I, Ssp I, Hpa I and combinations thereof are added and the resulting mixture is incubated under conditions suitable for restriction enzyme digestion. Digestion of the amplicon is then confirmed by any of a number of means known in the art, for example, by gel electrophoresis as shown in FIG. 2. Specifically, as shown in FIGS. 1 and 2, digestion of the HA amplicon with Sau 3AI and Spe I shows a specific banding pattern for variola, monkeypox, camelpox and vaccinia/cowpox. Similarly, digestion of the crmB amplicon with Dra I, Alw 44I, Ssp I and Hpa I results in a specific banding pattern for variola, monkeypox, camelpox, vaccinia and cowpox, allowing these viruses to be clearly distinguished from one another. Furthermore, as shown in FIG. 1(b), only monkeypox virus includes an Nla III restriction site, meaning that cleavage of an amplicon by this restriction enzyme clearly indicates that the sample in question includes monkeypox viral DNA.

Specifically, referring to FIGS. 1 and 2, if the sample tested contains Variola (Genbank Accession L22579), Camelpox (Genbank Accession AF438165), Vaccinia (Genbank Accession U94848) or Monkeypox DNA (Genbank Accession AF380138), incubation with SPOXHA5/SPOXHA3 and/or SPOXCRMB5/SPOXCRMB3 will result in the product of amplicon(s).

If the Orthopoxvirus DNA is Variola, digestion of the HA amplicon with Sau 3AI (at nucleotide 151462) and Spe I (at nucleotides 151483 and 151600) will produce restriction fragments of approximately 135 nts, 117 nts, 57 nts and 20 nts. Digestion of the crmB amplicon with Dra I (at nucleotide 183398), Alw 44I, Ssp I and Hpa I will produce two bands of approximately 168 nts and 98 nts.

If the Orthopoxvirus DNA is monkeypox, digestion of the HA amplicon with Sau 3AI (at nucleotide 159041) and Spe I (at nucleotide 159173) will produce restriction fragments of approximately 134 nts, 132 nts and 57 nts. Digestion of the crmB amplicon with Dra I, Alw 44I, Ssp I and Hpa I (at nucleotide 194885) will produce two bands of approximately 216 nts and 47 nts. Furthermore, as discussed above, only the monkeypox crmB amplicon includes an Nla III restriction site, producing fragments of 49 and 215 nts.

If the Orthopoxvirus DNA is camelpox, digestion of the HA amplicon with Sau 3AI (at nucleotides 163771 and 163884) and Spe I (at nucleotide 163909) will produce restriction fragments of approximately 135 nts, 113 nts, 57 nts and 24 nts. Digestion of the crmB amplicon with Dra I, Alw 44I, Ssp I (at nucleotide 202188) and Hpa I will produce two bands of approximately 147 nts and 119 nts.

If the Orthopoxvirus DNA is vaccinia, digestion of the HA amplicon with Sau 3AI (at nucleotides 149861 and 149953) and Spe I (at nucleotides 149861 and 149978) will produce restriction fragments of approximately 135 nts, 93 nts, 57 nts, 24 nts and 20 nts. Digestion of the crmB amplicon with Dra I, Alw 44I (at nucleotide 170867), Ssp I and Hpa I (at nucleotide 170923) will produce three bands of approximately 117-139 nts, 56 nts and 46 nts.

It is of note that the above-described primers are capable of binding to nucleic acid of Variola, Camelpox, Vaccinia and Monkeypox. It is of note that other suitable primers capable of amplifying the above-described genomic regions containing the restriction enzyme sites from one or more of the above Orthopoxviruses may also be used for identifying a specific Orthopoxvirus and are within the scope of the invention.

The kits of the invention comprise at least one pair of primers, comprising 12 or more consecutive nucleotides of ATGCCGGTACTTATGTATGTGC (SPOXHA5, SEQ ID NO: 1) and 12 or more consecutive nucleotides of TCTTGTCTGTTGTGGATTCT (SPOXHA3, SEQ ID NO: 2) for amplification of the region of the HA gene; and/or 12 or more consecutive nucleotides of TACCGGTCTCAGCGAATC (SPOXcrmB5, SEQ ID NO: 3) and 12 or more consecutive nucleotides of ACCGTCTCCGAATGCGGCAT (SPOXcrmB3, SEQ ID NO: 4) for amplification of the region of the crmB gene and a set of instructions, generally written instructions although electronic storage media (e.g., magnetic diskette or optical disk) containing instructions are also acceptable, relating to the use of the primers, hybridization conditions and the like. The kit may also include reagents for nucleic acid amplification, positive controls and suitable restriction enzymes as discussed herein. The kits may also include at least one positive control template, for example, VARV and MPXV HA and crmB amplicons, discussed below.

We developed diagnostic PCR-RFLP assays to detect and distinguish between variola and monkeypox, whose DNA is generally unavailable, and two other species of Orthopoxvirus, vaccinia and camelpox (Gubser, C. and Smith, G. L. J of Gen. Virol. 83,855-872(2002)). New primer sets for the haemagglutinin (HA) and the cytokine response modifier B (crmB) genes (Ropp, S. L. et al. J. Clin. Micro. 33, 2069-2076 (1995); Loparev, V. N. et al J. Clin. Micro. 39, 94-100 (2001)) were selected by aligning sequences entered into GenBank for all isolates of variola, monkeypox, camelpox, cowpox and vaccinia viruses. Amplicons of approximately 300 base pairs were identified which contained wholly conserved restriction enzyme sites to allow for RFLP analysis (FIG. 1). Relative sensitivity of the primer sets was determined using a serial dilution of DNA extracted from a vaccinia virus stock (VVT7 at $1\times10^8$ pfu/ml). Both primer sets were able to detect viral DNA equivalent to 7 pfu per reaction, a level, that is 10-100 fold more sensitive than the previously described sets (Ropp, S. L. et al. J. Clin. Micro. 33, 2069-2076 (1995); Loparev, V. N. et al J. Clin. Micro. 39, 94-100 (2001)).

To ensure our assay would be sufficiently robust for clinical samples regardless of sampling methods or shipping conditions, dilutions of vaccinia virus were sampled using cotton swabs and stored as dry swabs (CDC Guide D. Specimen collection guidelines.), or in 0.5 ml viral transport media for 18 hours at 4° C. Additional swabs were also sampled using a commercially available culture system and stored for 18 hours at 4° C., 30° C. or −20° C. to survey the effect of temperature of storage on sensitivity. DNA was extracted from each swab and assayed for the presence of both HA and crmB sequences. Under all regimes tested, no loss of sensitivity was detected.

In addition, we generated artificial templates to produce amplicons corresponding to HA and crmB sequences from variola and monkeypox viruses, to be used as positive controls in RFLP analysis (See FIG. 5; SEQ ID No. 5-8). As a test of our assay, vaccinia strain MVA T7, was used as an "Orthopoxvirus clinical sample" (test sample). DNA was extracted and PCR reactions for HA and crmB sequences were performed in parallel with reactions using vaccinia and camelpox genomic DNA and the cloned synthetic templates produced for both variola and monkeypox HA and crmB sequences. Appropriately sized amplicons were produced in both the HA and crmB reactions indicating the test sample was positive for Orthopoxvirus DNA (FIG. 2). Aliquots of all amplicons produced were digested with restriction enzymes along with the appropriate positive controls to identify the species of test sample (FIG. 2). Amplicons were directly sequenced to confirm identity.

The invention will now be described by way of examples; however, the invention is not limited by the examples.

PCR target sequence and primer selection

The hemagglutinin (HA) and cytokine response modifier B (crmB) genes have previously been utilized in the detection and differentiation of Orthopoxviruses (OPV) by PCR/RFLP analysis (Loparev et al., 2001; Ropp et al., 1995). Sequences for these two genes were compared among OPV identifying potential primers sets capable of generating short (~300 base pair) amplicons that contained restriction enzyme sites suitable for RFLP analysis. The following primers were identified and their location on the Variola Bangladesh genome (L22579) is given in parenthesis; SPOXHA5-5'-ATGCCGGTACTTATCTATGTG-3'(151327-151347)(SEQ ID No. 26), SPOXHA3-5'-TCTTGTCTGTTGTGGATTCT-3' (151656-

151637)(SEQ ID No. 2), SPOXcrmB5-5'-TACCGGTCT-CAGCGAATC-3'(183227-183244)(SEQ ID No. 3), SPOXcrmB3-5'-ACCGTCTCTCCGAATGCGACAT-3' (183493-183474)(SEQ ID No. 27). Primers were synthesized using standard phosphoamidite chemistry on a Beckman Oligo1000M (BeckmanCoulter, Mississauga, Ontario).

Viruses and DNA isolation

The orthopoxvirus strains and controls used in this study are summarized in Table 1. DNA was isolated from virus-infected cells, virions, serum, swabs and scab suspensions using QIAamp (Qiagen, Mississauga, Ontario) DNA purification kit according to the manufacturers instructions for buccal swabs with modifications. Briefly, samples or swabs were brought up to 400 µl with PBS containing 1 ug yeast tRNA (Sigma, Burlington, Ont). Qiagen protease and buffer AL were added and the samples incubated at 56° C. for 30 minutes followed by 95° C. for 15 minutes. 400 µl of ethanol was added to the sample, which was then applied to the supplied column. The column was then washed with 500 uL of buffer AW1 and centrifuged at 6,000 g for 1 minute followed by a second washing with 500 uL of buffer AW2 and centrifugation at 20,000 g for 3 minutes. The column was then dried by centrifugation at 6,000 g for 1 minute. Finally 50 µL of buffer AE was added to the column, incubated for 5 minutes at room temperature, followed by centrifugation at 6,000 g for 1 minute to elute the DNA which was subsequently stored at −20° C. until use.

PCR/RFLP analysis

Polymerase chain reactions were prepared using HotStarTaq PCR kits (Qiagen) following manufacturers instructions. Reaction mixtures (50 uL) were 1×PCR buffer with 2.5 mM $MgCl_2$, 200 uM each dNTP, 0.2 uM each primer, 2.5 units HotStarTaq DNA polymerase and 1 µl of DNA sample. PCR cycling conditions consisted of an initial activation step of 95° C. for 15 minutes followed by 40 cycles of 95° C. for 15 s, 50° C. for 30 s, 72° C. for 30 s. A final extension for 5 minutes at 72° C. was followed by an indefinite hold at 4° C. Products were analyzed on agarose gels and visualized by ethidium bromide staining. For RFLP analysis, the amplified DNA was purified using a PCR purification kit (Qiagen) according to manufacturers instructions and the DNA eluted in 30 ul final volume. Five microliters of this DNA was digested with 5 units of the appropriate restriction enzyme (New England Biolabs, Mississauga, Ontario) for 2 hours followed by electrophoresis agarose gel and visualized by ethidium bromide.

Determination of sensitivity and functionality in clinical samples

Vaccinia virus (VVT7) [$TCID_{50}=1\times10^8$ pfu/mL] was ten-fold serially diluted to $1\times10^{-2}$ pfu/ml in MEM (Invitrogen, Burlington, Ontario). OPV DNA from 100 ul aliquots of each dilution was isolated and PCR assays used to detect for the presence of OPV DNA. Virus dilutions were also allowed to absorb to an SW13 monolayer (ATCC, Manassas, Va.) for 1 hr at 37° C. after which the media was removed and the cellular monolayer lifted with a cotton swab. DNA was isolated from the swabs. DNA was also isolated from the scab and pustular fluid from a recent smallpox vaccine and the presence of OPV DNA determined by PCR analysis.

Construction of PCR/RFLP positive controls for Variola and Monkeypox

DNA sequences corresponding to VARV and MPXV HA (SEQ ID NO. 5 and 7) and crmB (SEQ ID NO. 6 and 8) amplicons were constructed from overlapping oligonucleotides (Table 2) which where annealed and subsequently filled in using T4 DNA polymerase (New England Biolabs, Mississauga, Ontario), amplified in a PCR reaction and cloned. Briefly, the primers for each set (VarHA1-84, VarHA167-65, VarHA148-250, VarHA330-231), (MPHA1-84, MPHA162-64, MPHA142-244, MPHA324-224), (VarcrmB1-115, VarcrmB207-95, VarcrmB185-299, SPOXcrmB3'), (MPcrmB1-115, MPcrmB207-95, MPcrmB187-295, SPOXcrmB3') were annealed by resuspending 30 pmol of each primer in 50 mM NaCl, 10 mM Tris-Cl (pH 7.9), 10 mM $MgCl_2$, 1 mM dithiothreitol in a total volume of 50 µl. The mixture was incubated at 95° C. for 3 minutes followed by 37° C. for 10 minutes and ice for 10 minutes. 5 ul of this mixture was added to 45 µl of 50 mM NaCl, 10 mM Tris-Cl (pH 7.9), 10 mM $MgCl_2$, 1 mM dithiothreitol, 0.2 mM dNTPs and 3 units of T4 DNA polymerase and incubated at 37° C. for 60 minutes. A PCR reaction was prepared with SPOXHA5/SPOXHA3 or SPOXcrmB5/SPOXcrmB3 primers with 5 µl of this annealed and extended product. The resulting PCR products were cloned into pCR4 TOPO vector (Clontech, Palo Alto, Calif.) followed by transformation into TOP10 cells. Individual colonies were selected from ampicillin containing plates, overnight cultures were grown, and plasmid preparations made using a Qiagen miniprep DNA kit. Identity of clones was confirmed by sequencing. Cassettes containing Hind III, Not I and Pst I sites were subsequently introduced into these clones by incorporating these sites into the following primers which were used in subsequent PCR reactions with the appropriate primer pair.

Ha cassette-
(SEQ ID No. 9)
5'ATGCCGGTACTTATATATGTGCATTCTTTATGACATCAAGCTTGCGGC

CGCTGCAGACTACAAATGATACT-3',

Var crmB cassette-
(SEQ ID No. 10)
5'TACCGGTCTCAGCGAATCCATCTYAAGCTTGCGGCCGCTGCAGAACGT

CGGAACTAACTATTAC-3',

MP crmB cassette-
(SEQ ID No. 11)
5'CGTCTCTGAATGCGGCATGATAGTATCATTCTTTGTCTGCAGCGGCCG

CAAGCTTTCGTTAACTGTTTG-3'

PCR products were cloned and confirmed by sequencing.

Results and Discussion

To address the perceived increased threat of a bioterrorism attack using Variola virus following the events of Sep. 11/2001 we undertook to develop PCR based diagnostic assays that would allow us to rapidly detect and identify this agent. As both the crmB and HA genes of OPV have previously been identified as suitable targets for PCR based diagnostics (Loparev et al., 2001; Ropp et al., 1995), we designed primer sets for these two genes that would produce smaller amplicons to allow both, a rapid PCR and the generation of synthetic positive controls, which still contained restriction enzymes sites suitable for RFLP analysis. The SPOXHA5/SPOXHA3 primer set was designed to produce an approximately 330 bp amplicon of the HA gene for most OPV, 329 bp for VARV and 323 bp for MPXV specifically. A Sau3AI site present at nucleotide 151462 of VARV strain Bangladesh (L22579) is wholly conserved among all these sequences currently entered in GenBank. VARV and MPXV are unique in OPV in that this is the only Sau 3AI site present in this amplicon, other members of the genus have either multiple sites or a single site present at another location. Digestion of VARV and MPXV HA amplicons with this enzyme will produce two fragments 139 bp and 188 or 194 bp characteristic of these two viruses. Further distinction between VARV and MPXV can be achieved by digestion of HA amplicons with Spe I (FIG. 1). Primers to amplify a region of the crmB gene (SPOXcrmB5/SPOXcrmB3) were also identified to produce 250-300 bp amplicons from OPV. VARV amplifies a product of 267 bp and MPXV a product of 264 bp. The other human tropic OPV produce fragments from 218 to 270 bp in size. Discrimination of VARV and MPXV from all others OPV can be achieved by Dra I and Nla III digestion respectively (FIG. 1). Both of these sites are wholly conserved in entries into GenBank and are unique to these species.

To determine the limit of sensitivity of these assays, a titration of OPV in MEM media was performed and viral DNA isolated. The presence of viral DNA was detected by PCR using both primer sets; the crmB and HA primer sets were capable of detecting OPV DNA corresponding to 0.002 and 0.02 pfu's respectively (FIG. 2a).

Figure 3:
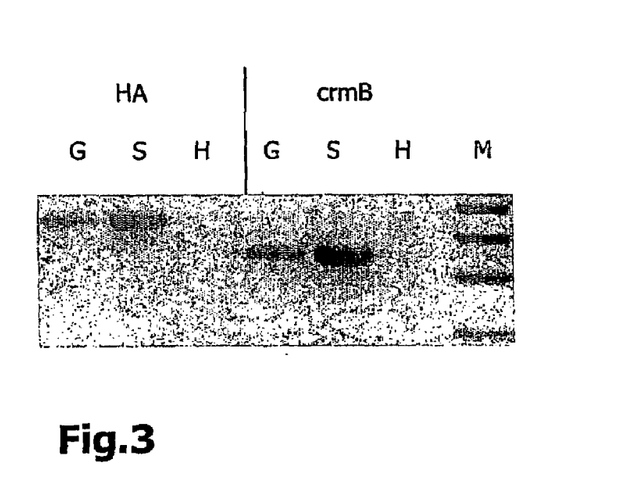
FIG. 3. Amplification of OPV DNA from a recent vaccinee. Samples isolated from the gauze covering the pustule (G) and from the scab crust (S) of a recent vaccinee were both assayed by PCR for OPV crmB and HA sequences. Negative control denoted by H, 100 to 400 bp markers are present on gel.

As samples for diagnosis of OPV would normally include scab crust or pustular material (Breman and Henderson, 2002, N. Engl. J. Med. 346:1300-1308; Centers for Disease Control and Prevention, 2003; Kelly et al., 2004, J Clin Microbiol. March;42(3):1373-5; Meyer et al., 2002, J. Clin. Microbiol. 40:2919-2921), material that may be confounding in an assay, total DNA was extracted from the scab crust and from the gauze used to cover the pustule of a recent vaccinee (Connaught Labs, Conn-Master 17633, lot#1556-14). The presence of OPV DNA was confirmed using both assays and the DNA was subsequently sequenced and most closely identified as Vaccinia strain Lister (FIG. 3). To mimic posterior tonsillor swabs that may be taken to detect virus in possibly exposed, but asymptomatic individuals, dilutions of vaccinia virus T7 stocks were also applied to SW13 monolayers, the virus was allowed to absorb to the monolayer, the infectious fluid removed and the monolayer (and absorbed virus) removed using a cotton swab. Total DNA was isolated and assayed by PCR. This method, although subject to losses from incomplete or inefficient viral absorption to the monolayer and losses due to material bound to the swab, still resulted in a detection limit of 0.02-0.2 pfu's or approximately 10 fold lower sensitivity than the direct isolation from stock (FIG. 2b).

To ensure specificity of the primer sets, DNA derived from sources (human genomic, monkey genomic, *Rickettsia rickettsia*, HSV type 1 and 2 and Varicella-zoster virus) that may be present in a VARV or MPXV test sample was assayed for OPV DNA. All sources were negative by both assays.

Figure 4:
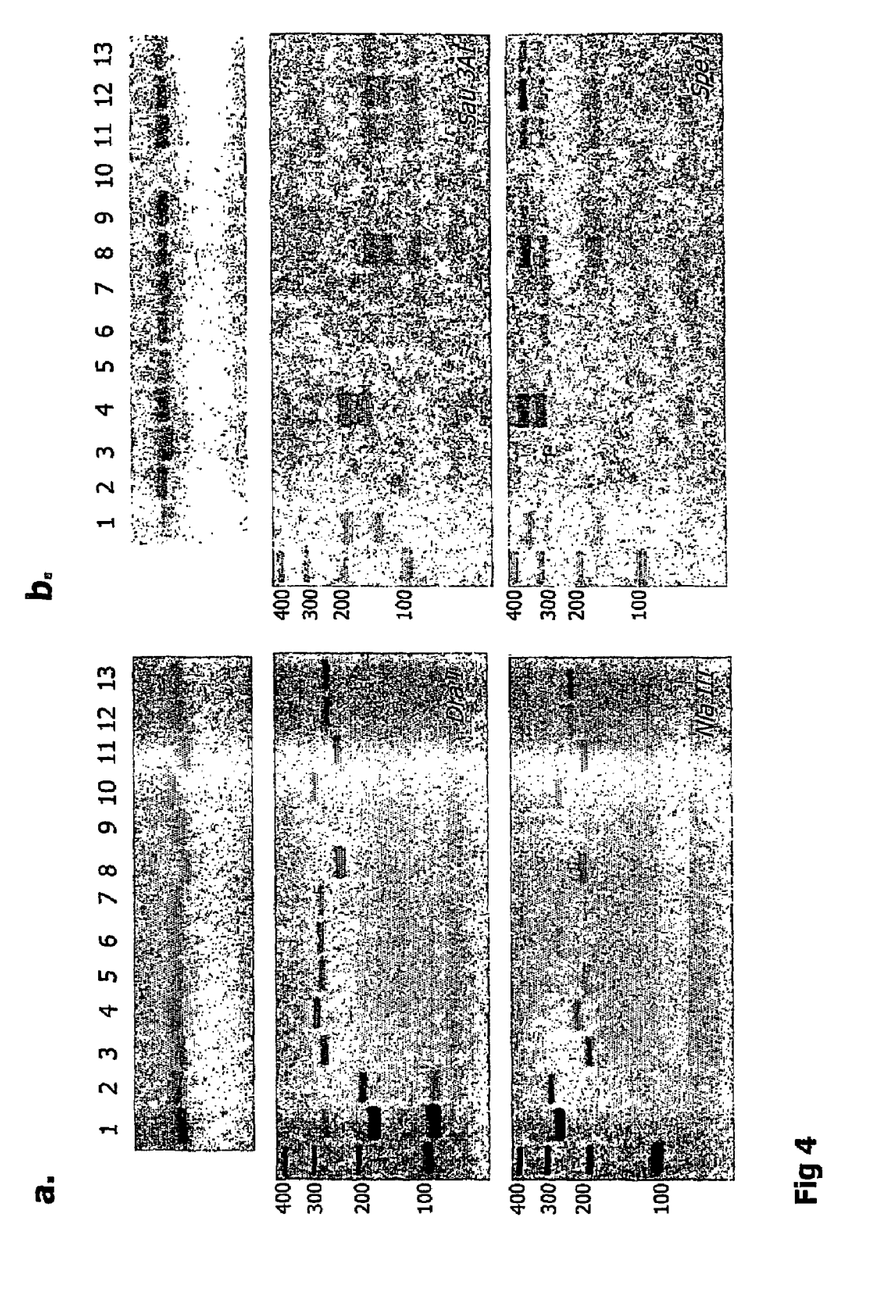

Synthetic amplicons to be used as positive controls for both the amplification and RFLP analysis were generated using overlapping large oligonucleotides. The original constructs contained sequences corresponding to GenBank entries for both VARV (L22579) and MPXV (AF380138) and were confirmed by standard dye terminator sequencing. These constructs were later modified with the insertion of a 19 bp sequence containing Hind III, Not I and Pst I restriction sites to allow simple discrimination between amplicons derived from a sample and those that may arise from contamination by positive control. FIG. 4 shows the result of amplification of both the original constructs (VC, MC, VH, and MH) and the modified constructs (VCN, MCN, VHN, and MHN) and their digestion with Pst I. Differentiation between products containing the original viral sequence and those containing the insert was possible on an agarose gel and with additional digestion by Pst I (or Hind III or Not I), the presence of the extraneous DNA in the modified positive controls can be confirmed.

A proficiency panel prepared by the European Network for Imported and Viral Diseases (ENIVD) (Niedrig et al., 2004, J. Clin. Microbiol. 42:1753-1755) was tested using both primer sets. The panel was provided as lyophilized material requiring suspension in water followed by DNA extraction and contained six different inactivated OPV (table 1) ranging in concentration from $10^7$ to $10^1$ genome equivalents. All viral genomes were detected in at least one assay (FIG. 4) and at all concentrations. The one sample which did not amplify in the HA assay, Cowpox Brighton Red, was subsequently found to lack the region corresponding to the SPOXHA3 primer.

We were fortunate to also have access to VARV DNA produced by the Centers for Disease Control, Atlanta as outlined in Table 1 that represents a portion of the exhaustive panel investigated by Ibrahim et al., (2003) and Kulesh et al., (2004). Our two assays were able to readily detect all VARV isolates provided and at all concentrations.

To address the practicality of RFLP analysis to differentiate OPV amplicons, samples from the ENIVD panel were amplified, restriction enzyme digested and electrophorised on an agarose gel. Along with these samples, the synthetic controls produced were also processed in a like manner. The results of this analysis are shown in FIG. 4. Digestion patterns produced by the authentic MPXV sample match those produced from the synthetic amplicons for MPXV and are distinguishable from the modified synthetic amplicons containing the 19 bp insert, while still allowing positive identification of the amplicon. The other OPV present have RFLP digestion patterns consistent with their predicted patterns.

Although RFLP analysis seems to have recently fallen out of favor as a diagnostic assay, as PCR followed by sequencing is now the 'gold standard' for molecular diagnostic identification (Ibrahim et al., 2003; Mackay et al., 2002), it can still provide relatively rapid information to identify a specific agent. Here we show that the amplicons produced in these assays from VARV or MPXV can be discriminated from each other and from other OPV by RFLP analysis. Due to the HA and crmB amplicons small size we were able to synthetically construct positive controls for both VARV and MPXV virus for use in PCR as well as RFLP. These controls were further modified to incorporate 19 bp inserts containing Hind III, Not I and Pst I restriction enzyme sites. These new constructs allow the both the PCR and RFLP assays to be controlled and also enable ready discrimination of amplicons that may be derived from contamination from the positive controls. This may be useful in facilities that do not have ready access to sequencing facilities. The implications of a positive VARV or MPXV test require that the utmost efforts be undertaken to ensure the accuracy of this diagnosis. In this context it is important to remember that histology and electron microscopy still can have a vital role OPV detection in particular and viral detection in general (Centers for Disease Control and Prevention, 2003; Hazelton and Gelderblom, 2003; Schoepp et al., 2004, Lab Invest. January; 84(1):41-8).

As we have seen with the HA amplification of Cowpox Brighton Red (and CPX, v00-1-20), it is possible for primers directed at well-conserved regions to fail on some isolates. With this in mind we targeted two well-separated (Massung et al., 1996, Virology 221:291-300) genes of OPV to minimize the generation of a false negative resulting from a genome deletion. Conversely, the generation of false positives, due to lab contamination, can be minimized with the use of the modified synthetic controls for both VARV and MPXV that are readily distinguishable from the wild-type sequence. Combined with sequencing and/or RFLP analysis, these tests and associated controls provide a simple, robust, sensitive and adequately controlled diagnostic tool for OPV molecular diagnostics.

While the preferred embodiments of the invention have been described above, it will be recognized and understood that various modifications may be made therein, and the appended claims are intended to cover all such modifications which may fall within the spirit and scope of the invention.

TABLE 1

Source of DNA samples.

| Virus or sample | Strain or isolate | Source |
| --- | --- | --- |
| Monkeypox virus | | ENIVD[a] |
| Camelpox virus | | ENIVD |
| Cowpox virus | Brighton | ENIVD |
| Cowpox virus | | ENIVD |
| Vaccinia virus | | ENIVD |
| Vaccinia virus | Modified | ENIVD |
| Ectromelia virus | | ENIVD |
| Vaccinia virus | MVA | NML[b] |
| Vaccinia virus | VVT7 | NML |
| Cowpox virus | | NML |
| Vaccinia virus | Lister | NML |
| Human genomic DNA | 293T | NML |
| Monkey genomic DNA | Vero E6 | NML |
| Rickettsia rickettsia | | NML |
| HSV type 1 | | NML |
| HSV type 2 | | NML |
| Varicella-zoster virus | | NML |
| Variola virus | 66-39 | CDC |
| Variola virus | 68-258 | CDC |
| Variola virus | 7124 | CDC |
| Variola virus | AFG | CDC |
| Variola virus | Garcia | CDC |
| Variola virus | Heidelberg | CDC |
| Variola virus | Higgins | CDC |
| Variola virus | Kembula | CDC |
| Variola virus | MS Lee | CDC |
| Variola virus | Shahzaman | CDC |
| Variola virus | Somalia | CDC |
| Variola virus | v74-227 Congo 9 | CDC |

TABLE 2

| Primer | Sequence 5'-3' |
| --- | --- |
| VarHA1-84 SEQ ID No. 12 | ATGCCGGTACTTATCTATGTGCATTCTTTATGACAT CAACTACAAATGATACTAATAAAGTAGATTATGAAG AATACTCTACAG |
| VarHA167-65 SEQ ID No. 13 | CTCAGAACTAGTTTCCGGTGAATGTGAAGATCCAGA TAGTATTATGTCTATAGTCGATTCACTATCTGTGTT TACAATCAACTCTGTAGAGTATTCTTCATAA |
| VarHA148-250 SEQ ID No. 14 | CACCGGAAACTAGTTCTGAGAAACCTGATTATATAA ATAATTTTAATTGCTCGTTGGTATTTGAAATCGCGA CTCCGGGACCAATTACTGATAATGTAGAAAA |
| VarHA330-231 SEQ ID No. 15 | TCTTGTCTGTTGTGGATTCTCCAGATGATGTACTTA CTGTATTAATGATATCACTAGTTATGTGACAGTGTC TGTATGATTTTCTACATTATCAGTAAT |
| MPHA1-84 SEQ ID No. 16 | ATGCCGGTACTTATATATGTGCATTCTTTATGACAT CGACTACAAATGATACTGATAAAGTAGATTATGAAG AATACTCCATAG |
| MPHA162-64 SEQ ID No. 17 | CTCAGAAATAGTTTCCGGTGTAGATCCAGATAGTAT TATGTCTATAGTCGATTCACTATCTGTATTTACAAT CAACTCTATGGAGTATTCTTCATAATC |
| MPHA142-244 SEQ ID No. 18 | CACCGGAAACTATTTCTGAGAAACCAGAGGATATAG ATAATTCTAATTGCTCGTCTGTATCGAAATCGCGAC TCCGGAACCAATTACTGATAATGTAGAAGA |
| MPHA324-224 SEQ ID No. 19 | TCTCGTCTGTTGTGGATTCTCCAGATGATGCATTTA CTGTATTAATGCTATCACTAGTGTATGTGACGGTGT CTGTATGGTCTTCTACATTATCAGTAATTGGT |
| VarcrmB1-115 SEQ ID No. 20 | TACCGGTCTCAGCGAATCCATCTTAACGTCGGAACT AACTATTACTATGAATCATACAGATTGCAATCCCGT ATTTCGTGAGGAATACTTCTCTGTCCTTAATAAGGT AGCAACT |
| VarcrmB207-95 SEQ ID No. 21 | AGAACCTTTGTTATTACATTTAATCTCAAAATTTAA AGTACACACCTTTGAAATATTTTGATATCTATTTTC TCCTGTAAAAAATCCTGAAGTTGCTACCTTATTAAG GACA |
| VarcrmB185-299 SEQ ID No. 22 | AAATGTAATAACAAAGGTTCTTCCTTCAAACAGCTA ACGAAAGCAAAGAATGATGACGGTATGATGTCGCAT TCGGAGACGGTAACTCTAGCGGGTGACTGTCTATCT AGCGTC |
| MPcrmB1-115 SEQ ID No. 23 | TACCGGTCTCAGCGAATCCATCTCAACGTCGGAACT AACTATTACCATGAATCATAAAGATTGTGATCCCGT CTTTCGTGCAGAATACTTCTCTGTCCTTAATAATGT AGCAACT |
| MPcrmB207-95 SEQ ID No. 24 | GATGAATCTTTGTTGTTACATTTAATCTCGAAATTC AGAGTACATATCTTTGAAGTATTCTGATATCTATTT TCTCCTGTAAAGAATCCTGAAGTTGCTACATTATTA AGGAC |
| MPcrmB187-295 SEQ ID No. 25 | AAATGTAACAACAAAGATTCATCTTCCAAACAGTTA ACGAAAACAAAGAATGATACTATCATGCCGCATTCA GAGACGGTAACTCTAGTGGGCGACTGTCTATCTAGC GT |

The invention claimed is:

1. A method of detecting and identifying an orthopoxvirus within a sample comprising:

adding to the sample reagents for nucleic acid amplification and at least one pair of primers capable of amplifying at least one region of the orthopoxvirus genome, said pair of primers being selected from the group consisting of 12 or more consecutive nucleotides of ATGCCGG-TACTTATGTATGTGC (SPOXHA5, SEQ ID NO: 1) and 12 or more consecutive nucleotides of TCTTGTCT-GTTGTGGATTCT (SPOXHA3, SEQ ID NO: 2) when said region of the orthopoxvirus genome is gene HA; and 12 or more consecutive nucleotides of TACCG-GTCTCAGCGAATC (SPOXcrmB5, SEQ ID NO: 3) and 12 or more consecutive nucleotides of ACCGTCTCCGAATGCGGCAT (SPOXcrmB3, SEQ ID NO: 4) when said region of the orthopoxvirus genome is gene crmB;

incubating the sample under conditions suitable for nucleic acid amplification thereby producing an amplicon if the sample contains orthopoxvirus;

adding at least one restriction enzyme selected from the group consisting of: Sau 3AI, Spe I, Dra I, Hpa I, Ssp I, Alw 44I, Nla III, and combinations thereof; and determining if restriction enzyme digestion of an amplicon has occurred.

2. The method according to claim 1 wherein restriction enzyme digestion of an amplicon is determined by gel electrophoresis.

3. The method according to claim 1 wherein the orthopoxvirus is identified based on the restriction enzyme digestion pattern.

* * * * *